United States Patent [19]

Bala

[11] Patent Number: 5,406,939
[45] Date of Patent: Apr. 18, 1995

[54] ENDOSCOPE SHEATH

[76] Inventor: Harry Bala, 7 Corey Dr., South Barrington, Ill. 60010

[21] Appl. No.: 195,556

[22] Filed: Feb. 14, 1994

[51] Int. Cl.$^6$ ............................................. A61B 1/00
[52] U.S. Cl. ..................... 128/4; 206/316.1; 206/438; 206/63.5; 206/363; 206/368; 604/163; 604/263
[58] Field of Search .......................... 128/4, 6, 844, 11; 604/163, 171, 263, 172; 206/316.1, 303, 305, 306, 438, 439, 440, 63.5, 69, 363, 368; 433/29, 116

[56] References Cited

U.S. PATENT DOCUMENTS

| | | | |
|---|---|---|---|
| 4,646,722 | 3/1987 | Silverstein et al. | 128/4 |
| 4,823,949 | 4/1989 | Bala | 206/306 |
| 4,846,344 | 7/1989 | Bala | 206/306 |
| 5,069,337 | 12/1991 | Bala | 206/306 |

Primary Examiner—Richard J. Apley
Assistant Examiner—Beverly A. Meindl
Attorney, Agent, or Firm—Gerstman, Ellis & McMillin, Ltd.

[57] ABSTRACT

A protective sheath for an endoscope probe comprises a pair of elongated plastic sheets peripherally sealed together at the sides and distal ends thereof, while being unsealed at the proximal ends. A first of the sheets is transparent, having greater optical clarity than the other sheet. The other sheet has better frictional slip characteristics than the first sheath. Also, an intermediate plastic sheet may be provided between the pair of plastic sheets, so that the endoscope probe slides into the sheath between the other sheet and the intermediate sheet. The intermediate plastic sheet may have better frictional slip characteristics than the first sheet, to render easier the advancement of the probe into the sheath. The intermediate sheet terminates short of the distal ends of the sheet pair.

19 Claims, 1 Drawing Sheet

ENDOSCOPE SHEATH

BACKGROUND OF THE INVENTION

Sheaths for medical and dental probes are rapidly entering into frequent use to avoid contamination of such probes and cross infection of subsequent patients. For example, in Bala U.S. Pat. Nos. 4,823,949; 4,846,344; and 5,069,337, by way of example, inexpensive sheaths for oral thermometers, anal thermometers, and other probes are disclosed. These sheaths are made of heat-sealed sheets of plastic, packaged in an outer sheath which may have a paper side, with both the probe sheath and the outer package sheath being manufactured in a single sealing process.

There also is a need to provide inexpensive, disposable sheaths for various endoscopes, for example intraoral or dental cameras, as well as other endoscopes for penetration into the body interior through an anal route, an oral route, or the like. Such endoscopes have a distal end with an optical view opening which usually carries a lens, for viewing internal body areas from the endoscope proximal end.

It is highly desirable for the endoscope to be positioned in such a protective sheath with its lens or opening on the distal end facing an optically clear plastic sheet section of the sheath. However, the most desirable types of optically clear plastic film are somewhat tacky on their surface, so that if a sheath of such material is constructed, it can be difficult to insert the endoscope into the sheath. It should be remembered that, typically, a fairly tight fit is required between the endoscope and the sheath, particularly at the distal tip, where the sheath most desirably covers the lens in a tight manner so that folds or wrinkles of the sheath material are not found in front of the distal lens or opening of the endoscope.

Because of this, the best, optically clear plastic films have not been effectively useable in endoscope sheaths. Rather, less tacky plastic films have been used, which are less clear than the best, optically clear films, so that while the endoscope may be more easily inserted into the sheath, the image that the endoscope can project from its distal optical system to the user is less than optimum because of the reduced clarity of the sheath film material.

By this invention, a plastic film sheath for endoscopes is provided in which an optically clear plastic wall can be provided for the distal endoscope optics, but the sheath exhibits reduced frictional resistance to advancement of the endoscope into the sheath, for improved handling of the sheath and endoscope without any significant reduction in the quality of what is seen through the optical system thereof.

DESCRIPTION OF THE INVENTION

By this invention a protective sheath for an endoscope probe is provided, which sheath comprises a pair of elongated plastic sheets which are peripherally sealed together at the sides and distal ends thereof, while being unsealed at the proximal ends thereof to permit entry of an endoscope probe. By this invention, a first of the sheets of the pair is transparent, and has greater optical clarity than the other sheet of the pair of peripherally sealed plastic sheets. Also, the other sheet has better frictional slip characteristics than the first sheet.

The first sheet of greater optical clarity may be preferably made of polyethylene. Certain grades of polyethylene are quite optically clear, although possessing a greater surface tack than the less clear grades of polyethylene which are used to make plastic bags and the like. Typically, the first, optically clear sheet may be made of a polyethylene formulation which is substantially free of slip improving additives, which are added to many formulations for the very purpose of eliminating the tack which is found in the clearest polyethylene formulations.

The other sheet of the sheath may be made of a poly(ethyl-methyl acrylate) plastic (EMA), for example, or a polyethylene formulated to have greater slip characteristics, and consequently lower optical clarity, than the first sheet. Such a sheath may be made in accordance with any conventional design, for example in accordance with the teachings of Bala U.S. Pat. No. 4,823,949, to provide a sheath where first side is optically clear and typically somewhat tacky, and the other side is less clear but with less tack. Thus, the endoscope probe may be more easily inserted into the sheath, typically with a relatively tight fit at the tip. The probe is positioned so that its distal optical port "looks" through the optically clear first sheath.

Both the EMA plastic and the polyethylene formulations are commercially available.

Such a two layer sheath can be effective with respect to endoscope probes which have a matte finish or a knurled surface along the majority of its length. Such surfaces have lower frictional characteristics, which permit them to be easily inserted into the preferred designs of the above-described sheaths.

However, some metal or plastic endoscope probes having a smooth finish are still advanceable only with difficulty into sheaths where a first of the walls is optically clear and more tacky than the other wall, which is less clear but which has greater slip characteristics. For such endoscope probes, another embodiment of this invention is preferably used, in which an intermediate plastic sheet is positioned between the pair of plastic sheets described above and sealed to at least one of the pair of sheets, and preferably both, adjacent their respective lateral edges. The intermediate sheet is spaced from the distal ends of the two original plastic sheets discussed above, so that an endoscope can be inserted from the sheath proximal end between the other sheet described above and the intermediate sheet. The endoscope probe is advanced until a distal tip portion of the endoscope engages the distal end portion of the first sheet in a manner which is spaced from the intermediate sheet, which is shorter. By this invention, the intermediate plastic sheet has better frictional slip characteristics than the first sheet of high optical clarity.

Thus, when the endoscope probe is inserted between the other sheet and the intermediate sheet, it is easily advanced, since both of those sheets have better frictional slip characteristics than the first sheet of higher optical clarity. It is only at the distal tip area where the first sheet becomes exposed to the endoscope tip, since the intermediate sheet is spaced from the distal end portion of the sheath. The endoscope probe is easily advanced, but when it reaches its completely advanced position, the distal optical port thereof faces only the optically clear first sheet, so that good visualization can be achieved through the endoscope, along with the protection provided by the sheath.

The first sheet may be made of polyethylene of improved optical clarity compared with the intermediate sheet and the other sheet, which may be made, for example, of EMA plastic, or a polyethylene of better slip characteristics.

The first sheet preferably extends proximally beyond the proximal end of the other sheet at the rear end of the sheath. This facilitates the opening of the proximal or rear end of the sheath for easy insertion of the endoscope probe. Also, the first sheet and the intermediate sheet may be transversely sealed together adjacent the proximal ends thereof, to prevent an endoscope probe from entering the sheath between the first sheet and the intermediate sheet.

It is also preferable for the first sheet to be made of a somewhat stretchable material, like polyethylene, so that the portion of the first sheet which covers the distal optical port may be stretched by the fit of the particular endoscope probe into the sheath distal tip, to provide a smooth, tight surface over the optical port. If desired, a clip may be applied to the sheath and endoscope distal tip to facilitate this stretching and seating of the first sheet over the endoscope distal optical port, to provide the best optical visualization, combined with the protection imparted by the sheath.

DESCRIPTION OF SPECIFIC EMBODIMENTS

Figure 2:
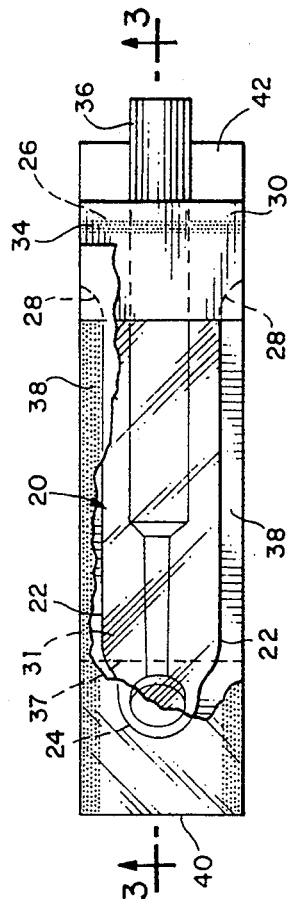
FIG. 2 is a plan view, with portions broken away, of the assembled probe sheath of FIG. 1; showing the sheath containing an endoscope probe.
Figure 3:
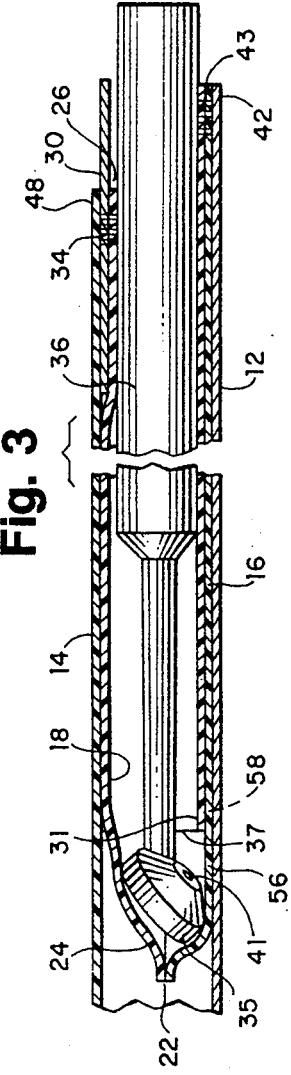
FIG. 3 is a sectional view taken along line 3—3 of the probe sheath of FIG. 2, showing the sheath containing a probe.
Figure 1:
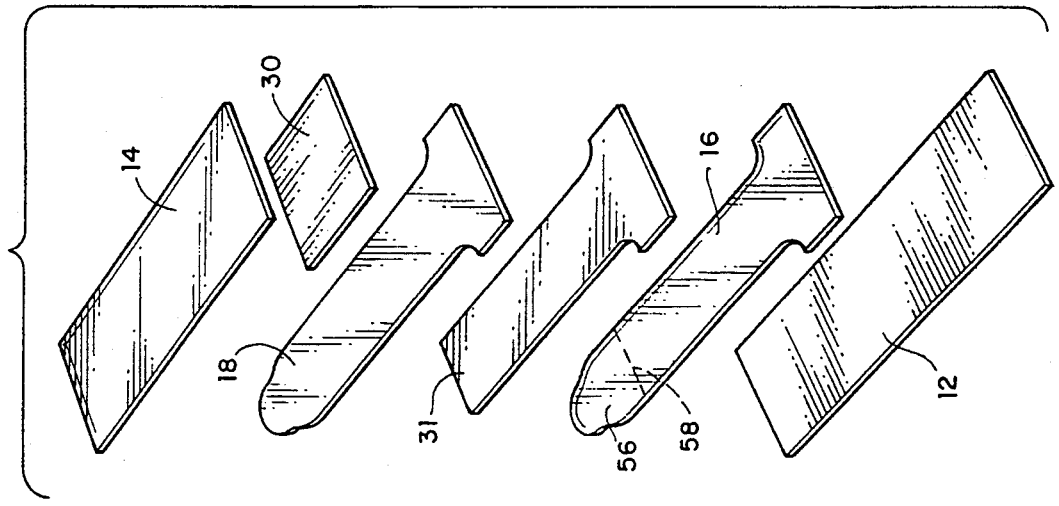
FIG. 1 is an exploded perspective view of the probe sheath in accordance with this invention.

Referring to FIGS. 1-3, a packaged sheath is disclosed in which backing web 12 may originally be part of a continuous web and associated sheaths, with the respective sheaths being separated by fold lines in the backing web for separation by tearing.

The separate parts of the packaged sheath are disclosed in FIG. 1. Backing web 12 defines the bottom layer of the assembly, while upper web 14 defines the top layer, forming the package for the sheath. Between these layers are a pair of flat side sections 16, 18 of the probe sheath 20. First sheet 16 and other sheet 18 are joined together by the sealing together of plastic sheet portions along a heat seal line 22 (FIG. 2) followed by the optional cutting away of outer flashing material. Heat seal line 22 curves around the closed distal end 24 of the sheath, so that the distal end and sides of probe sheath 20 are closed. End 26 of probe sheath 20 is open, to permit the endoscope probe 36 to be inserted, as shown in FIGS. 2 and 3.

Tab member 30 is also provided, being made of a material which is heat sealed to sheet 18 of the probe sheath.

An intermediate sheet 31 is also provided between sheets 16, 18. As shown, sheet 31 terminates at its distal end 37 short of the distal ends 24 of first sheet 16 and other sheet 18, to be spaced from the distal end 24 of the sheath of this invention. Intermediate sheet 31 is peripherally sealed to sheets 16, 18 by seal line 22, except that sheet 31 terminates short of distal end 24 of sheets 16, 18.

In this embodiment, first sheet 16 is made of a high clarity polyethylene, which material may be substantially free of slip-improving additives which tend to reduce the clarity of the polyethylene when added thereto. Thus, first sheet 16 exhibits an increased amount of tack and has relatively lower friction characteristics than many other forms of polyethylene which contain such additives.

Sheets 18 and 31 may be made of EMA plastic, a commercially available material which has better slip characteristics than the material of sheet 16, for lower friction advancement of an endoscope probe into the sheath between layers 18, 31. However, commercially available EMA plastic is distinctly less clear than the plastic of sheet 16, exhibiting a slight cloudiness.

As endoscope probe 36 is advanced into sheath 20, the distal optical tip 35 of probe 36 passes beyond the distal end 37 of sheet 31. Optical tip 35 of endoscope probe 36 may be of any conventional arrangement, typically comprising an aperture 41 with a lens for conveying an image the length of probe 36 electronically or optically to a screen, or to film, as may be desired. Also, lights may be optionally carried in the tip of probe 36 in accordance with various designs of conventional dental camera probes and the like.

Since optical tip 35 extends beyond the end 37 of sheet 31, light from an area being observed by the probe has to only pass through the single layer of optically clear sheet 16, which is separated from sheet 31 in the distal area 24. Thus, endoscope probe 36 is easily advanced between sheets 18 and 31 until its optical tip 35 extends beyond sheet 31 into engagement with tip portion 56 of sheet 16. The optical probe tip 35 can be positioned so that the optical port 41 in the tip faces sheet 16 in the distal area 24, so that the combination of easy advancement along the sheath and clear observation through the endoscope probe is achieved.

As an alternative embodiment, sheet 31 can be eliminated, so that the endoscope probe is advanced between sheets 16, 18. This simplified version of the sheath of this invention can be effectively used particularly with endoscope probes which have a roughened outer surface by some texturing technique, which has the effect of reducing their friction.

Preferably the distal tip 24 of sheath 20 is made to be initially slightly smaller than the distal tip 35 of probe 36 so that the plastic material is stretched as the probe tip enters the distal end area of the sheath. This facilitates a tight stretching of sheet 16 across the observation port of the endoscope probe tip which can improve the observing conditions through the sheath, as especially seen in FIG. 4.

The particular design of the probe sheath and package shown is similar to the design of probe sheath described in U.S. Pat. No. 4,823,949, but for the particular differences described herein.

Tab member 30 is sealed to the other sheet 18 along a transverse area 34 to cause the tab member to be in adherent relation thereto. Portion 28 of seal line 22 defines a funnel portion as shown which seals together flat sides 16, 18, 31 and also may help seal tab 30 to the sheath. This leaves open end 26 bracketed by the funnel shaped seal lines 28 between flat sides 18 and 31, providing a space for insertion of probe 36 as shown in FIG. 3 and elsewhere. Sheets 16 and 31 are sealed together at proximal end area 43, to assure that the probe enters the sheath between layers 18 and 31. Sheet 16 is also releasably sealed to backing web 12 through the same sealing area 43. Backing web 12 may be a plastic coated paper to permit participation in such a seal.

As shown particularly in FIG. 2, the two outer packaging webs 12, 14 are peripherally sealed to each other at side areas 38. Typically the nature of side seal areas 38 is such that they may be easily peeled apart for opening, in the standard manner of a peel seal. End 40 of webs 12, 14 may have a transverse seal therebetween if desired, or the webs 12, 14 may be open at that end.

Most of flat sheet 16 may be adhered to backing web 12 with a light tack seal to keep the sheath 20 in a desired position, while permitting easy removal thereof. The natural tack of sheet 16 may suffice. On the other hand, preferably, no such tack seal is provided between upper web 14 and sheet 18.

As shown in FIGS. 2 and 3, one may insert an endoscope probe 36 into sheath 20 so that it occupies the position shown. After probe 36 has been inserted, one may remove the outer packaging of the probe sheath by grasping end portion 42 of backing web 12 and end 48 of upper web 14, which is typically not attached to tab 30, peeling the two sheets away toward end 40 to expose probe sheath 20. Or, one can grasp the endoscope 36 and peel away outer sheet 14 or outer sheet 12 individually.

Thus, the sheath of this invention provides the protection of a sheath to patients, while at the same time maintaining good optical clarity through the sheath for maximum effective endoscope probe performance. The probe may be easily advanced through the sheath for the reasons described above.

Figure 4:
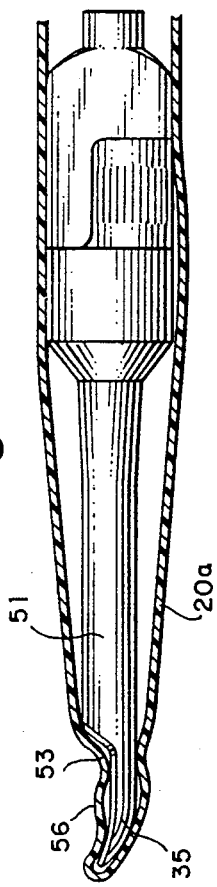
FIG. 4 is an elevational view of the probe sheath of this invention containing a different design of endoscope probe.

Referring to FIG. 4, a different design of endoscope probe is shown, being surrounded by a modified sheath 20a. Endoscope probe 51 has a distal tip and recess 53 with its optical aperture being defined in that recess. The probe sheath 20a of this invention may be made in a manner similar to that described above but with slightly differing dimensions, so that the probe sheath is stretched as the endoscope tip 35 presses into it, to stretch the optically clear layer 56 of the sheath across the optical aperture of the endoscope probe.

As an alternative embodiment, transparent sheet 16 may be eliminated except for its tip portion 56, distal to line 58. Transparent tip portion 56 may be sealed to end 37 of sheet 31. This forms an equivalent structure to that of FIG. 3, with the rest of layer 16 that overlaps sheet 31 being absent.

The above has been offered for illustrative purposes only, and is not intended to limit the scope of the invention of this application, which is as defined in the claims below.

That which is claimed is:

1. A protective sheath for an endoscope probe which comprises a pair of elongated plastic sheets peripherally sealed together at the sides and distal ends thereof and unsealed at the proximal ends thereof, a first of said sheets being transparent and having greater optical clarity adjacent its distal end than the other sheet, the other sheet having better frictional slip characteristics than the first sheet adjacent said first sheet distal end.

2. The sheath of claim 1 in which said first sheet is made of polyethylene.

3. The sheath of claim 2 in which said other sheet is made of a material selected from the group consisting of EMA plastic and a polyethylene having greater slip characteristics and lower optical clarity than said first sheet.

4. The sheath of claim 2 in which said first sheet is made of polyethylene which is substantially free of slip improving additives.

5. The sheath of claim 1 which is packaged in an openable outer sheath.

6. The sheath of claim 1 in which an intermediate plastic sheet is positioned between said pair of plastic sheets and sealed to at least one of said pair of sheets adjacent their respective lateral edges, said intermediate sheet being spaced from said distal sheet ends, whereby an endoscope probe can be inserted from the proximal sheath end between said other sheet and the intermediate sheet, and advanced until a distal tip portion of said endoscope probe engages a distal end portion of said first sheet while spaced from said intermediate sheet, said intermediate sheet having better frictional slip characteristics than said first sheet.

7. The sheath of claim 6 in which said first sheet is made of polyethylene, and said intermediate sheet and other sheet are made of EMA plastic.

8. The sheath of claim 6 in which said first sheet extends proximally beyond the proximal end of said other sheet.

9. The sheath of claim 6 in which said first sheet and intermediate sheet are transversely sealed together adjacent proximal ends thereof, to prevent an endoscope probe from entering the sheath between said first sheet and said intermediate sheet.

10. The sheath of claim 1 in which said first sheet is shorter than said other sheet, said first sheet having a proximal end sealed to an intermediate plastic sheet, which intermediate sheet is peripherally sealed to said other sheet.

11. A protective sheath for an endoscope probe which comprises a pair of elongated plastic sheets peripherally sealed together all the sides and distal ends thereof, and unsealed at the proximal ends thereof, a first of said sheets being made of polyethylene and being transparent with greater optical clarity adjacent its distal end than the other sheet, the other sheet being made of a material selected from the group consisting of EMA plastic and polyethylene, said other sheet having greater frictional slip characteristics and lower optical clarity than said first sheet adjacent said first sheet distal end, said sheath being packaged in an openable outer sheath.

12. The sheath of claim 11 in which said first sheet is made of polyethylene which is substantially free of slip improving additives.

13. A protective sheath for an endoscope probe which comprises a pair of elongated plastic sheets peripherally sealed together at the sides and distal ends thereof, and unsealed at the proximal ends thereof, a first of said sheets being transparent and having a greater optical clarity than the other sheet, the other sheet having better frictional slip characteristics than the first sheet, said sheath also comprising an intermediate plastic sheet positioned between said pair of plastic sheets and sealed to at least one of said pair of sheets adjacent their respective lateral edges, said intermediate sheet being spaced from said distal sheet ends, whereby an endoscope probe can be inserted from the proximal sheath end between said other sheet and the intermediate sheet, and advanced until a distal tip portion of said endoscope probe engages a distal end portion of said first sheet while spaced from said intermediate sheet, said intermediate sheet having better frictional slip characteristics than said first sheet, said first sheet extending proximally beyond the proximal end of said other sheet, and in which said first sheet and intermediate sheet are transversely sealed together adjacent proximal ends thereof, to prevent an endoscope probe from entering the sheath between said first sheet and said intermediate sheet.

14. The sheath of claim 13 in which said first sheet is made of polyethylene.

15. The sheath of claim 14 in which said intermediate sheet and said other sheet are made of EMA plastic.

16. The sheath of claim 1 in which said first sheet has a distal end portion of greater optical clarity than other portions of said first sheet, the other first sheet portions having better frictional slip characteristics than said distal end portion.

17. The sheath of claim 1 in which said first sheet has said greater optical clarity along its entire length.

18. The sheath of claim 11 in which said first sheet has a distal end portion of greater optical clarity than other portions of said first sheet, the other first sheet portions having better frictional slip characteristics than said distal end portion.

19. The sheath of claim 11 in which said first sheet has said greater optical clarity along its entire length.

* * * * *